United States Patent [19]

Palva et al.

[11] Patent Number: 4,731,325

[45] Date of Patent: Mar. 15, 1988

[54] ARRAYS OF ALTERNATING NUCLEIC ACID FRAGMENTS FOR HYBRIDIZATION ARRAYS

[75] Inventors: Airi M. Palva, Helsinki; Tuula M. Ranki; Hans E. Söderlund, both of Espoo, all of Finland

[73] Assignee: Orion-yhtymä, Espoo, Finland

[21] Appl. No.: 694,325

[22] Filed: Jan. 24, 1985

[30] Foreign Application Priority Data

Feb. 17, 1984 [FI] Finland ................................ 840655

[51] Int. Cl.⁴ .......................... C12Q 1/70; C12Q 1/68; C12P 19/34; G01N 33/566
[52] U.S. Cl. .......................................... 435/6; 435/5; 435/7; 435/91; 436/501; 536/26; 536/27; 536/28; 935/77; 935/78
[58] Field of Search .................. 435/5, 6, 91, 7; 935/6, 935/23, 32, 72, 73, 78, 77; 536/28, 29, 26, 27; 436/501

[56] References Cited

U.S. PATENT DOCUMENTS

| | | | |
|---|---|---|---|
| 4,293,652 | 10/1981 | Cohen | 536/27 X |
| 4,366,246 | 12/1982 | Riggs | 435/317 X |
| 4,486,539 | 12/1984 | Ranki et al. | 436/504 |
| 4,563,417 | 1/1986 | Albarella et al. | 935/78 X |

OTHER PUBLICATIONS

Morrow, J. F., et al., PNAS, 71 No. 5: 1743-1747 (1974).
Wellauer, P. K., et al., Journ. Mol. Biol., 105: 487-505 (1976).
Lee, A. S., et al., Science, 196: 189-192 (1977).
Tamashiro, J. C., et al., Journ. Virol., 42 No. 2: 547-557 (1982).

*Primary Examiner*—Sidney Marantz
*Assistant Examiner*—Jack Spiegel
*Attorney, Agent, or Firm*—Burns, Doane, Swecker & Mathis

[57] ABSTRACT

The invention is related to improved nucleic acid reagents comprising arrays of nucleic acid fragments and combinations of such fragments. The preparation of such fragments by recombinant DNA techniques and their use in sandwich hybridization methods is also described. By making different combinations of the nucleic acid fragments—some labeled and some affixed to solid carriers, it is possible to create kits for the identification of e.g. veneral diseases.

The improved nucleic acid reagents comprise two series of at least two alternating nucleic acid fragments, which are homologous to sequences in the nucleic acid to be identified, one of the series being labeled and one affixed to a solid carrier. Nucleic acid fragments belonging to different series must not be homologous to each other.

Sandwich hybridization tests performed with arrays of nucleic acid fragments are at least four times as sensitive as sandwich hybridization tests performed with reagents belonging to the prior art.

22 Claims, 13 Drawing Figures

FIG.1

PRIOR ART

ARRAYS OF ALTERNATING NUCLEIC ACID FRAGMENTS FOR HYBRIDIZATION ARRAYS

The invention relates to improved nucleic acid reagents comprising an array of nucleic acid fragments and to combinations of such improved reagents. The invention also relates to methods for the preparation of nucleic acid reagents comprised of an array of clones, and combinations of such nucleic acid reagents, by recombinant-DNA techniques, and to their use for the identification of nucleic acids by hybridization methods.

Various hybridization methods have commonly been used for the identification and study of nucleic acids. Some examples are the direct hybridization methods, in which the sample containing the nucleic acid to be identified is either in a solution (Brautigam et al., J. Clin. Microbiol., 1980, 12, 226–234 and the British Patent Publication No. 2,019,408) or affixed to a solid carrier (U.S. Pat. Nos. 4,139,346, 4,302,204, 4,358,535, 4,395,486, the British Patent Publications Nos. 2,034,323, 2,095,833, the European Patent Publications Nos. 62,286, 62,237 and 61,740), and is detected by using one labeled nucleic acid reagent which hybridizes with the nucleic acid to be identified.

Other known hybridization methods include the two-step sandwich hybridization method presented by Dunn and Hassell in Cell, 12, 23–36, 1977, and the one-step sandwich hybridization methods presented in the European Patent Publication No. 79,139. For the identification of the nucleic acids by the sandwich methods two separate nucleic acid reagents are needed to detect the nucleic acids present in the sample solution. One of these reagents is affixed to a solid carrier and the other is labeled.

Nucleic acid reagents, both those affixed to a solid carrier and those which are labeled, are characterized in that their base sequence is complementary, or nearly complementary, to the nucleic acid to be identified, i.e. homologous. The nucleic acid reagents used are either natural nucleic acids as such or as fragments of them. The fragments are produced, for example, by using restriction enzymes. Nucleic acid reagents have also been prepared synthetically or by recombinant-DNA techniques. Natural plasmids (U.S. Pat. No. 4,358,535), nucleic acids from bacteriophages (U.S. Pat. No. 4,543,535), ribosomal RNA and messenger RNA (U.S. Pat. No. 4,302,204), or nucleic acid from different viruses (Stalhandske et al., Curr. Top. Microbiol. Virol. 104, 1983) have been used as the nucleic acid reagents. The whole virus genome has been used for identifying, for example, parts belonging to the different viruses in the messenger RNA of a hybrid virus (Dunn and Hassell, Cell, 12, 23–36, 1977). Nucleic acid reagents have also been prepared by using recombinant-DNA techniques (U.S. Pat. Nos. 4,395,486 and 4,359,535, the European Patent Application No. 79,139 and the British Patent Publication No. 2,034,323 and the European Patent Application No. 62,286). Nucleic acid reagents produced by recombinant-DNA techniques have been used either in such a way that the replicated defined DNA fragment has been purified out from the DNA of the vector, or as recombinant-DNA molecules linked to different vectors. The previously used nucleic acid reagents produced by recombinant-DNA techniques are made up of one continuous identifying nucleic acid fragment or of several separate clones.

We have developed new, more sensitive nucleic acid reagents, comprising at least two series of alternating arrays of nucleic acid fragments prepared from either one or several segments homologous to the nucleic acid to be identified.

Nucleic acid reagents which comprise such arrays of nucleic acid fragments are in sandwich hybridization tests at least twice as sensitive as the previously used nucleic acid reagents. By using the nucleic acid reagents according to the invention, or their combinations, it is possible to identify smaller amounts of nucleic acids than previously, and they are especially well applicable for sandwich hybridization methods.

Figure 1:
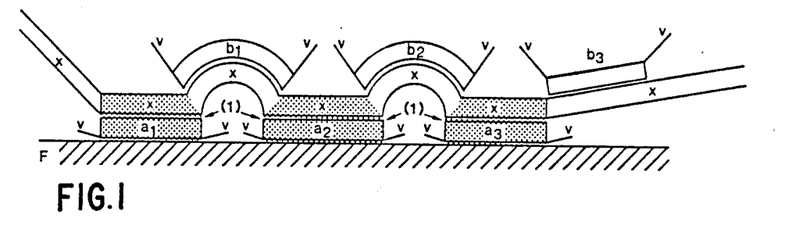
FIG. 1 shows an array of sandwich hybrids.
Figure 2:
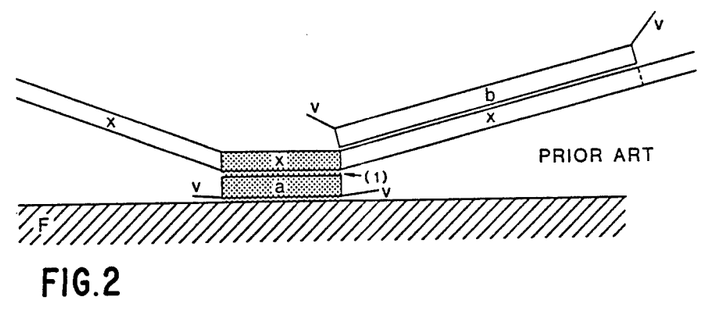
FIG. 2 depicts a sandwich hybrid of the prior art.

The higher sensitivity of the nucleic acid reagents according to the invention in sandwich hybridization methods is in part based on the fact that the use of several probes increases the quantity of labeled hybrids on the solid carrier. There may be labeled vector-derived nucleic acid along with every hybridizing probe (FIGS. 1 and 2). In FIGS. 1 and 2, v represents vector-derived DNA, x the nucleic acid to be identified, b the labeled probe, a the identifying nucleic acid reagent affixed to the solid carrier, and F the filter. When several probes are used, the quantity of labeled, vector-derived nucleic acid parts increases, and more label is bound to the hybrids being formed. The hybrids are thus more easily detectable.

When the array of nucleic acid fragments according to the invention are used in sandwich hybridization methods, at least two, or as shown in FIG. 1, three, identifying nucleic acid fragments are affixed to the solid carrier. In this case the different areas of the nucleic acid strand x to be detected may hybridize to the nucleic acid fragments affixed to the solid carrier, for example $a_1$, $a_2$, and $a_3$, at one or several points, depending on the degree of reaction. When the reaction reaches its final stage, a situation according to FIG. 1 may be produced, in which the sample strand forms a loop or loops to which the probe or probes, for example, $b_1$ and $b_2$ in FIG. 1, hybridize. At this time the distance of the vector-derived nucleic acid parts from the hybridization joining point (1) d creases (FIG. 1), and the hybrid is more stable than the hybrid formed by one reagent pair (prior art) shown in FIG. 2, this hybrid being of the same size as the total area of the array of nucleic acid fragments. The vector-derived parts of a hybrid formed from one reagent pair are easily broken by, for example, mechanical strain, such as shaking. In such a case the label already bound to the hybrid escapes.

Since the improved nucleic acid reagents according to the invention are more sensitive than previously used nucleic acid reagents, they are suitable for demonstrating chromosomal rearrangements and hereditary diseases.

Our invention relates to nucleic acid reagents comprising an array of nucleic acid fragments, their combinations, their preparation, and their use for the detection of nucleic acids in hybridization methods. The characteristics of the invention are shown in the distinguishing features of the claims, and the invention is described in greater detail in the following description and in the a companying drawings, in which FIG. 6 shows an array of sandwich hybrids.

The arrays of nucleic acid reagents can be prepared synthetically. In this case the fragments from the two alternating series of arrays of nucleic acid fragments, must not be homologous to each other. But they must be sufficiently homologous to alternating sites in the nucleic acids to be identified. These fragments can easily be prepared by fully automatic machines after characterization of the nucleic acid sequence of the nucleic acid to be identified.

The nucleic acid reagents according to the invention are composed of separate, or joined, or both separate and joined array of nucleic acid fragments.

The arrays of nucleic acid fragments may be joined to a vector, contain parts of vectors, or be totally devoid of vector parts.

The nuclei acid fragments used have a minimum length of 15 nucleotides. There is no actual upper limit for length, but it is advantageous to use fragments having a length of 20–5000 nucleotides. The nucleic acid fragments according to the invention are derived either from the genome to be identified or from one part of the genome, for example from a relatively large clone representin a certain part of the genome. The arrays of nucleic acid fragments according to the inventio can thus be prepared from several independent genome areas which are not directly adjacent. The arrays of nucleic acid fragments thus prepared are combined and used for the same reagent. The arrays of nucleic acid fragments can also be isolated from a DNA which is not identical to the nucleic acid to be identified but sufficiently homologous, so that a stable hybrid is formed between the reagent and the nucleic acid to be identified. The preparation of suitable arrays of nucleic acid fragments: is by no means limited to the isolation of suitable nucleic acid fragments from the genome. There are available many equally useful methods to prepare such arrays of fragments. The man skilled in the art can prepare arrays of nucleic acid fragments by synthetic or semisynthetic methods.

Figure 3:
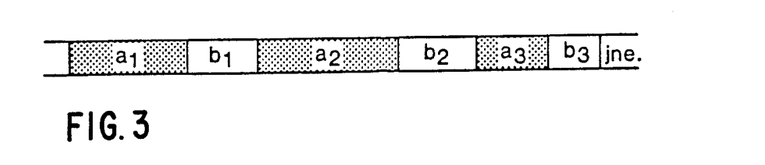
FIG. 3 shows the sites of two alternating series of nucleic acid fragments in a nucleic acid which has been selected for the preparation of an array of nucleic acid reagents according to the invention.
Figure 4:
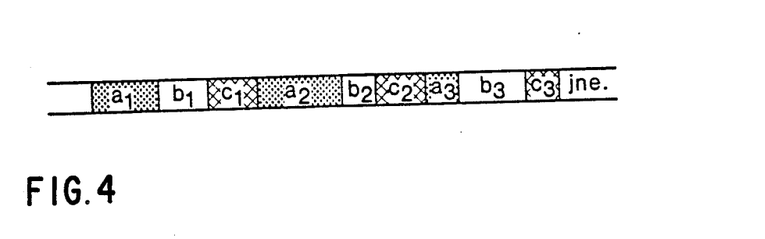
FIG. 4 shows the corresponding sites of three alternating series of arrays of nucleic acid fragments.

The reagents are isolated in such a way that at least two series of alternating nucleic acid fragments $a_1$, $a_2$, $a_3$, etc., and $b_1$, $b_2$, $b_3$, etc., are obtained. The nucleic acid fragments belonging to the series $a_1$, $a_2$, $a_3$, etc. are composed of fragments situataed close to but not adjacent to one another. The nucleic acid fragments belonging to the series $b_1$, $b_2$, $b_3$, etc. are also composed of nucleic acid fragments situated close to but not adjacent to one another. The nucleic acid fragments belonging to the series $a_1$, $a_2$, $a_3$, etc. and those belonging to the series $b_1$, $b_2$, $b_3$, etc. must be homologous to each other. It is preferable that the nucleic acids belonging to the series $a_1$, $a_2$, $a_3$, etc. and those belonging to the series $b_1$, $b_2$, $b_3$, etc. are isolated in such a way that every second fragment belongs to the a-series and every second to the b-series, as shown in FIG. 3. In FIG. 3, $a_1$, $a_2$, $a_3$, and $b_1$, $b_2$, $b_3$ are arrays of nucleic acid fragments sufficiently homologous to the nucleic acid to be identified. It is, of course, possible that even a third nucleic acid fragment series, $c_1$, $c_2$, $c_3$, etc., is isolated from the same nucleic acid, as shown in FIG. 4. It is preferable that the alternating two nucleic acid reagents follow one another directly, but this is no absolute prerequisite for the invention.

Figure 5A:
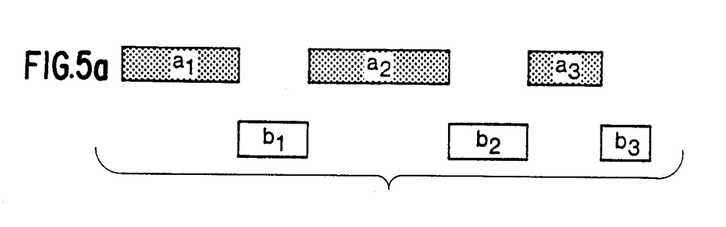
FIG. 5 shows an array of nucleic acid fragments according to FIG. 3 separate (a), joined together (b) and both separate and joined together (c)
Figure 5B:
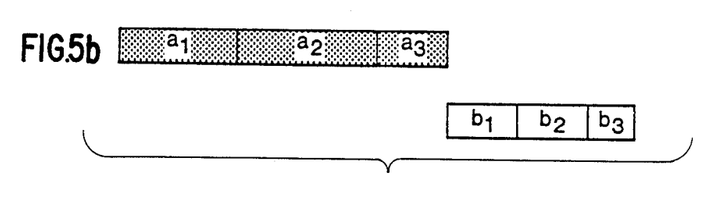
Figure 5C:
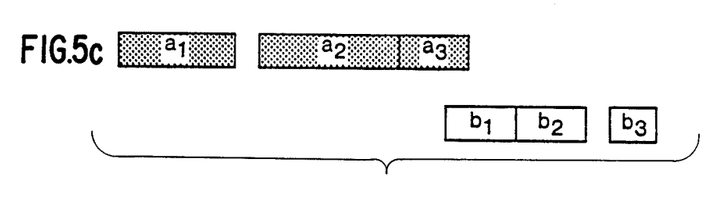

The nucleic acid fragment series described above can be used either as separate fragments $a_1$, $a_2$, $a_3$, etc., and $b_1$, $b_2$, $b_3$, etc. (FIG. 5a) or joined together into longer strands $a_1$–$a_2$–$a_3$, etc., and $b_1$–$b_2$–$b_3$, etc. (FIG. 5b). It is, of course, possible to prepare all kinds of intermediate forms such as, for example, an a-series in which $a_1$ is a separate fragment and $a_2$–$a_3$ are joined together, and in the b-series, for example, $b_1$–$b_2$ are joined together and $b_3$ is separate, etc., as shown in FIG. 5c.

Figure 6A:
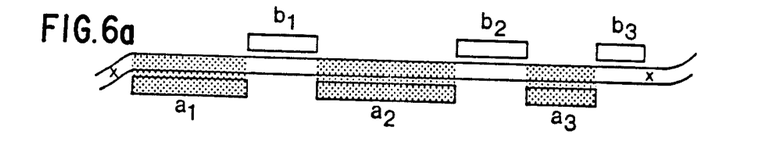
FIG. 6a shows an array of sandwich hybrids which is formed when separate fragments are used.
Figure 6B:
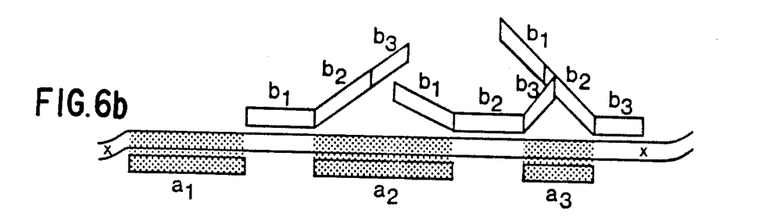
FIG. 6b shows an array of sandwich hybrid which is formed when joined b-fragments are used.
Figure 6C:
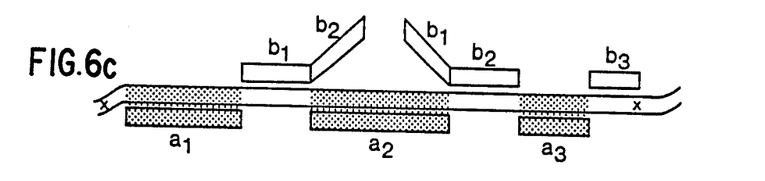
FIG. 6c shows an array of sandwich hybrids which is formed when both separate and joined b-fragments are used.

FIG. 6 depicts various arrays of sandwich hybrids. FIG. 6a shows an array of sandwich hybrids in which the arrays of nucleic acid fragments are separate. FIG. 6b shows an array of hybrids in which the labeled array of nucleic acid fragments are joined together. FIG. 6c depicts a case in which an array of sandwich hybrids is formed from both joined and separate labeled arrays of nucleic acid fragments. In FIG. 6, x represents the nucleic acid to be identified; $b_1$, $b_2$, and $b_3$ represent the labeled probe, and $a_1$, $a_2$, and $a_3$ represent arrays of nucleic acid fragments affixed to a solid carrier.

Nucleic acid fragments which belong to the b-series can, for example, be labeled in such a way that a labeled nucleic acid reagent is obtained, i.e. the probe B. The nucleic acid reagents which belong to the a-series can be affixed to a solid carrier in such a way that a nucleic acid reagent A bound to a solid carrier is obtained. It is, of course, alternatively possible to prepare a labeled nucleic acid reagent A, and a corresponding nucleic acid reagent B bound to a solid carrier.

Figure 7:
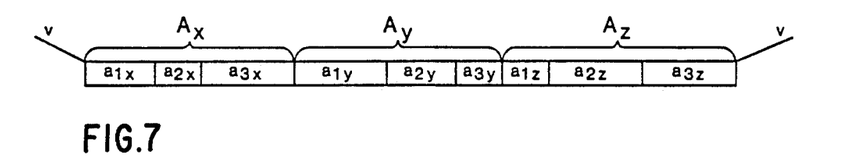
FIG. 7 shows an array of nucleic acid reagents which identify different nucleic acids.

Such nucleic acid pairs A and B, or B and A, labeled and respectively affixed to a solid carrier can be prepared for several different nucleic acids to be identified. They can be combined into suitable nucleic acid reagent combinations, which are composed of different nucleic acid reagent pairs $A_1$ and $B_1$, $A_2$ and $B_2$, $A_3$ and $B_3$, etc., or $B_1$ and $A_1$, $B_2$ and $A_1$, $B_2$ and $A_3$, etc. Reagents containing arrays of nucleic acid fragments which identify different nucleic acids can also be combined so that a probe $A_x$–$A_y$–$A_z$ is obtained, which, for example, comprises an array of nucleic acid fragments $(a_1-a_2-a_3)_x$–$(a_1-a_2-a_3)_y$–$(a_1-a_2-a_3)_z$, as shown in FIG. 7, in which $a_{1x}$, $a_{2x}$ and $a_{3x}$ are arrays of nucleic acid fragments $A_x$ which identify nucleic acid x; $a_{1y}$, $a_{2y}$ and $a_{3y}$ are arrays of nucleic acid fragments $A_y$ which identify nucleic acid y; $a_{1z}$, $a_{2z}$ and $a_{3z}$ are arrays of nucleic acid fragments $A_z$ which identify nucleic acid z, and v is a vector-derived nucleic acid part. Joined arrays of nucleic acid fragments can, of course, also be used as separate fragments, as suitable mixtures.

Figure 8A:
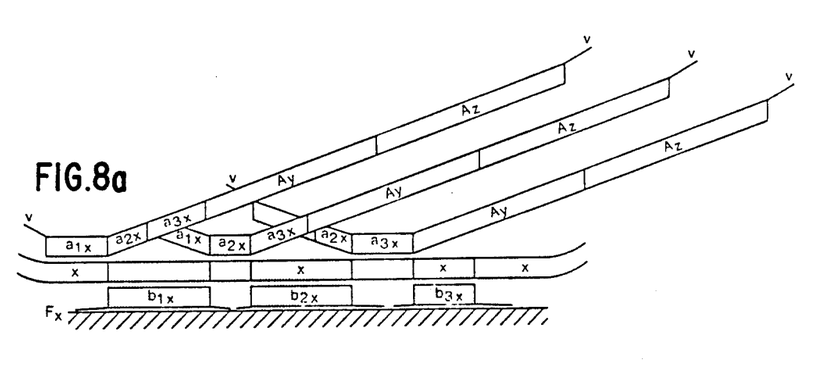
FIG. 8 shows an array of sandwich hybrids which are formed when the array of nucleic acid reagents according to FIG. 7, identifying different nucleic acids, are used.
Figure 8B:
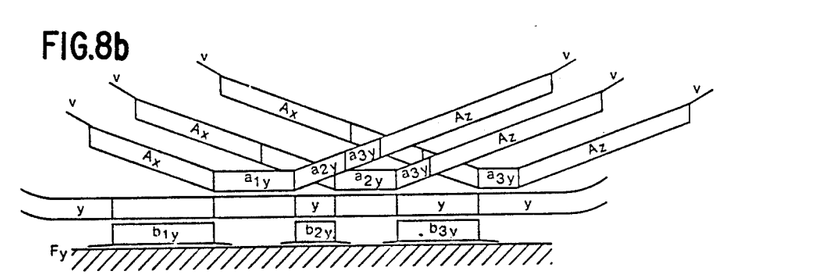
Figure 8C:
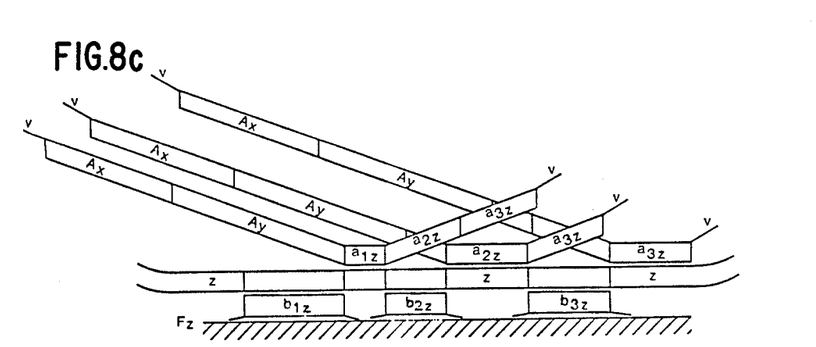

The arrays of sandwich hybrids according to FIG. 8 are obtained by using the reagents shown in FIG. 7. If simultaneous identification of several different nucleic acids is desired, it is, of course, necessary to use separate filters, as shown in FIG. 8. FIG. 8a shows a solid carrier identifying the nucleic acid x, FIG. 8b a solid carrier identifying the nucleic acid y, and FIG. 8c a solid carrier identifying the nucleic acid z. In FIGS. 8a, 8b and 8c, $b_{1x}$ and $b_{2x}$ are arrays of nucleic acid fragments affixed to a solid carrier and identifying the nucleic acid x; $b_{1y}$ and $b_{2y}$ are arrays of nucleic acid fragments affixed to a solid carrier and identifying the nucliec acid y; and $b_{1z}$ and $b_2$ are arrays of nucleic acid fragments affixed to a solid carrier and identifying the nucleic acid z; and x, y and z are the nucleic acids to be identified. $F_x$, $F_y$ and $F_z$ are the respective solid carriers or filters, $A_x$–$A_y$–$A_z$ is a probe which identifies all the three nucleic acids simultaneously, if separate solid carriers are used.

The above-described nucleic acid fragment series, reagents and reagent combinations can be prepared by recombinant-DNA techniques known per se. A number of nucleic acid fragments of different lengths are generated, by using restriction enzymes, from the nucleic acid to be identified or from a part representing it. If the restriction map of the genome to be identified is known, it is possible to select from the genome the suitable adjacent fragments, generated by using restriction enzymes, and the fragments are isolated and amplified by using recombinant DNA techniques.

When an unknown genome is involved, an intermediate stage can be used in the preparation of the reagents, in such a way that a relatively large restriction fragment is cloned, this fragment is mapped, and the arrays of nucleic acid fragments series $a_1$, $a_2$, $a_3$, etc., and $b_1$, $b_2$, $b_3$, etc., are produced on the basis of the information thus obtained.

It is, of course, possible to use combinations of the above methods and to use several large separate cloned restriction fragments as starting material, and to prepare several separate series, which are combined to form suitable combinations.

It is advantageous to prepare the nucleic acid fragment series $a_1$, $a_2$, $a_3$, etc., and $b_1$, $b_2$, $b_3$, etc., according to the invention by using recombinant-DNA techniques in such a way that the series a is cloned into one vector, for example into the plasmid pBR322, and whereas the series b is cloned into another suitable vector, which does not have sequences in common with the previous vector. The bacteriophage M13 is an example of such a second advantageous vector. The fragments belonging to the series a can be joined to one another, and the joined series can be cloned into one vector. For example, $a_1$–$a_2$, joined together, can be cloned as a continuous insert into the same pBR322 vector. In a corresponding manner it is possible to prepare a reagent series $b_1$–$b_2$. In the cloning it is preferred to use vectors to which very large inserts of foreign DNA can be joined. For example, lambdaphage and cosmid vectors are suitable for this purpose.

Thus, two reagent pairs comprising arrays of nucleic acid fragments are needed in the sandwich hybridization method according to the invention, a reagent labeled with the label substance to be identified, i.e. a probe, and a so-called filter reagent affixed to a solid carrier.

Most commonly, radioactive isotopes are used for labeling the probes. For example in the British Patent Publication No. 2,034,323, the U.S. Pat. Nos. 4,358,535 and 4,302,204 the following isotopes are used: $^{32}P$, $^{125}I$, $^{131}I$ and $^{3}H$. In the European Patent Publication No. 79,139, the isotope $^{125}I$ is used. Nucleic acid probes have also been modified in different ways and labeled with, e.g. fluorescent labels (French Patent Publication No. 2,518,755). Also enzymatic or enzymatically measureable labels are used (the British Patent Publication No. 2,019,408, the European Patent Publication No. 63,879 and the French Patent Publication No. 2,519,005). The European Patent Publications Nos. 70,685 and 70,687 describe a light-emitting label and labeling method, and the French Patent Publication No. 2,518,755 describes an immunologically measurable label.

The lanthanide chelates described in U.S. Pat. No. 4,374,120, especially europium, can be used as label substances. Also the biotin-avidin label substance described by Leary et al. (PNAS 80, 4045–4049, 1983) is suitable as a label. A few examples of labels which can be used for the labeling of nucleic acid reagents according to the invention are mentioned above, but it is evident that there will be developed new, improved label substances which are also suitable for the labeling of arrays of nucleic acid fragments according to the invention.

The carriers suitable for filter reagents include various nitrocellulose filters (U.S. Pat. No. 4,358,535 and the British Patent Publication No. 2,095,833). The DDR-Patent Publication No. 148,955 desribes a method of binding nucleic acids chemically to the carrier (paper). U.S. Pat. Nos. 4,359,535 and 4,302,204 describe chemically modified papers which can be used as solid carriers. Other alternatives include nylon membranes and modified nitrocellulose filters. But it is evident that there will be developed new materials which will be even more suitable for use as solid carriers according to the invention. It is, of course, possible to use also other solid carriers, such as various chromatography matrices such as triazine- or epoxy-activated cellulose, latex, etc. In principle, there are no other limitations to the selection of the solid carrier than those to be described below. It has to be possible to affix nucleic acid in a single-stranded form to the solid carrier so that these single-stranded nucleic acids can hybridize with the complementary nucleic acid. The solid carrier must also be easy to remove from the hybridization solution, or the hybridization solution must be easy to remove from the solid carrier. Also, the probe must not adhere to the carrier material itself so that it cannot be washed off.

The above-described combinations of the arrays of nucleic acid reagent pairs A and B, or B and A, labeled and affixed to a solid carrier respectively, and from such nucleic acid pairs made for the identification of different nucleic acids it is possible to assemble a combination $A_x$ and $B_x$, $A_y$ and $B_y$, $A_z$ and $B_z$.

These combinations can be used for the simultaneous identification of the nucleic acids x, y and z by sandwich hybridization methods.

The sample is treated in such a way that the nucleic acids are released into the hybridization solution, and they are rendered single-stranded. The hybridization is carried out in a hybridization solution, to which both the nucleic acid reagents affixed to a solid carrier and the labeled ones are added. When hybridization has taken place, the filters are lifted from the hybridization solution, if filters have been used as solid carriers. If chromatography matrices, latex, or the like have been used, the hybridization solution is removed. The solid carriers are rinsed with a suitable washing solution. The arrays of sandwich hybrids formed (FIGS. 8a, 8b, 8c) are detected by methods known per se. The radioactive label is measured, for example, by autoradiography, by a scintillation counter or by a gamma-counter. For example, an enzymatic label is identified after, for example, a color reaction, by photometry or on the basis of a precipitate. Lanthanide chelates can be detected by a so-called "time resolved fluorescence" method. An immunological label is detected by immunological methods suitable for the purpose.

Several different mixtures can be used as the hybridization solution; the alternatives presented in the European Patent Publication No. 79,139 and U.S. Pat. No. 4,302,204 are mentioned as examples. It is, of course, also possible to use other hybridization mixtures. The hybridization takes place at a temperature of 0°-80° C., but is advantageous to use, for example, a temperature of 65° C. Sufficient hybridiztion may occur in a very short period, but it is advantageous to use hybridization periods of, for example, 12–20 hours.

The two-step sandwich hybridization method is carried out in principle in the same manner, but in this case the nucleic acid reagent affixed to a solid carrier is first added to the hybridization solution. When the hybridization has taken place, the solid carrier is washed and a second hybridization is carried out in which the labeled nucleic acid reagent is present.

Figure 9A:
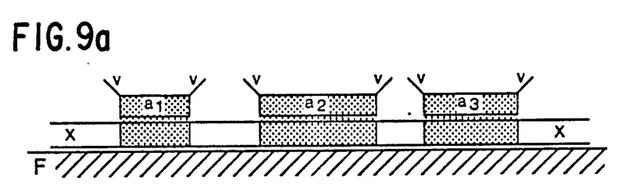
FIG. 9 shows an array of hybrids formed by a direct hybridization method.
Figure 9B:
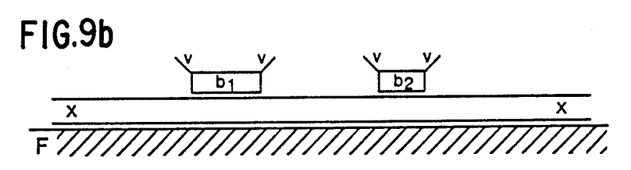
Figure 9C:
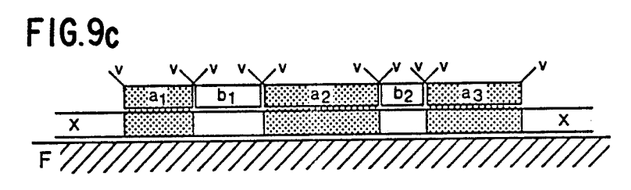
Figure 10:
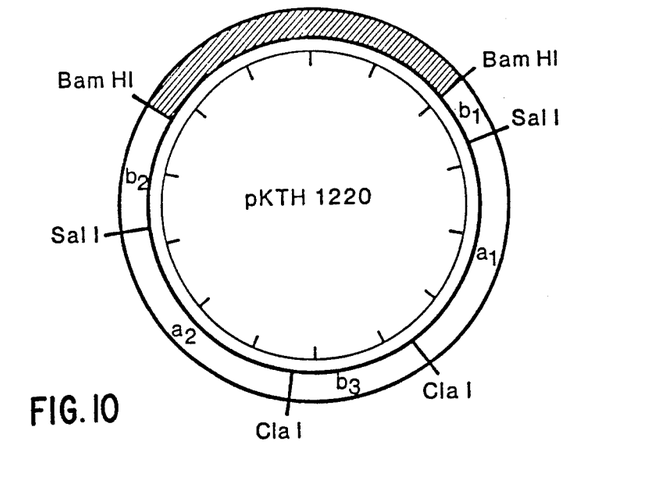
FIG. 10 shows the recombinant plasmid pKTH1220.
Figure 11:
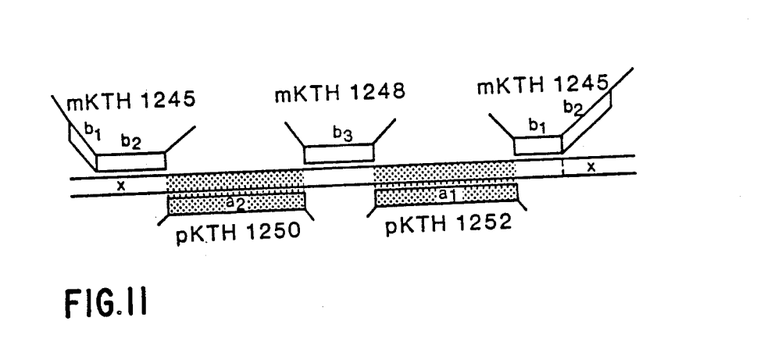
FIG. 11 shows an array of sandwich hybrids which is formed when an array of nucleic acid fragments prepared from the recombinant plasmid pKTH1220 are used.

The above-described labeled nucleic acid reagents or reagent combinations $A_x$, $A_y$, $A_z$, etc., and $B_x$, $B_y$, $B_z$, etc., can, of course, be used in direct hybridization methods. In such a case the nucleic acid sample in a solution must be divided for each nucleic acid x, y and z to be identified or, if the sample is affixed to a solid carrier, a separate sample affixed to a carrier must be prepared for each sample. The formed array of hybrids (FIG. 9) is detected by methods known per se. In FIG. 9, F represents the solid carrier, i.e. the filter, x the nucleic acid to be identified, and v the vector-derived parts. The labeled probes used are $a_1$, $a_2$ and $a_3$ (FIG. 9a), $b_1$ and $b_2$ (FIG. 9b), and $a_1$, $b_1$, $a_2$, $b_2$; $a_3$ (FIG. 9c).

As already described above, various combinations of nucleic acid reagents can be made up from the arrays of nucleic acid fragments according to the invention. It is possible by using these combinations to identify several different nucleic acids simultaneously. Arrays of nucleic acid fragments homologous to the different nucleic acids to be identified can be used as separate fragments in the mixtures or joined together in such a manner that one probe identifying several different nucleic acids is obtained. Nucleic acid reagents affixed to a solid carrier must, of course, be kept separate in order for the identification to be successful.

Hybridization using arrays of nucleic acid fragments can be used for identifying various human, animal and plant pathogenic microorganisms. By the method it is possible to identify microorganisms present in foodstuffs, such as clostridia, salmonellae, staphylococci, which cause food poisonings. The method is suitable for the identification of contaminants present in water, such as enterobacteria and enteroviruses. Since the sandwich hybridization test using arrays of nucleic acid fragments is a quantitative method, it is applicable to, for example, the detection and measurement of gene amplification. This characteristic is significant in, for example, the detection and treatment of cancer. The formation of a stable array of hybrids requires that the homologous sequences of the probe reagent and the filter reagent are located within a moderate, preferably less than 5 kilobase (kb), distance from each other in the sample strand. If changes with respect to the distance between these two areas do occur, the change is cleary observable by this method. Therefore the method is also suitable for the detection of changed mRNA, chromosomal rearrangements, the rearrangement of immunoglobulin genes for expression, and hereditary diseases. It is thus possible to construct various reagent combinations from the arrays of nucleic acid fragments. For example, for the identification of the causative agents of venereal diseases it is possible to prepare kits which include a probe which contains arrays of nucleic acid fragments which identify gonorrhea, syphilis, herpes and chlamydiae. The identification is in this case possible by using separate filters for gonorrhea, syphilis, herpes and chlamydiae.

The invention relates in particular to arrays of nucleic acid fragments comprising the recombinant plasmids pKTH1220 and pKTH1271. The recombinant plasmid pKTH1220 comprises, in the plasmid vector pBR322, DNA of *Chlamydia trachomatis* L2 which is specific to the Chlamydiae. This recombinant plasmid is cloned into the host *Escherichia coli* K12 HB101. The recombinant plasmid 1271 comprises, in the plasmid vector pBR325, DNA from the cytomegalovirus AD169. This recombinant plasmid is cloned into host *Escherichia coli* K12 HB101. The hosts containing the recombinant plasmids pKTH1220 and pKTH1271 have been deposited at the culture collection Deutsche Sammlung von Mikroorganismen (DSM), Griesebachstrasse 8, D-3400 Gottingen, West Germany. The number of the deposit containing the recombinant plasmid pKTH1220 is DSM2825 and the number of the deposit containing the recombinant plasmid pKTH1271 is DMS2826. The deposits will be freely available once the patent application has been made public.

The invention is described in greater detail in the following examples. These examples must not, however, be understood as limiting the protective scope of the invention. The structure of the nucleic acid (DNA and RNA) is similar whether the question is of a nucleic acid derived from a eucaryotic or a procaryotic cell. For this reason the principles presented in the examples are equally well applicable to the nucleic acids of animals (man included), plants and microbes or viruses. Thus the reagents according to the invention can be used to detect the nucleic acids of man, animals, plants, microbes and viruses. The arrays of nucleic acid fragments can be prepared synthetically, too. The sequence of nucleic acids to be identified can be characterized and homologous arrays of fragments prepared by automatic nucleic acid preparing machines.

EXAMPLE 1.

(a) Arrays of nucleic acid reagents from Chlamydia trachomatis and their preparation DNA fragments suitable for the diagnostics of the Chlamydia trachomatis group were prepared from the DNA of Chlamydia trachomatis serotype L2. The DNA was isolated and fragmented by known methods, and the resulting DNA fragments were cloned into the plasmid pBR322 and transferred to the host organism Escherichia coli K12 HB101, by known methods. A gene bank of the *Chlamydia trachomatis* L2 bacterium was obtained as a result of the cloning, i.e. a large number of recombinant plasmids, each having a separate BamHI restriction fragment of DNA derived from chlamydiae. For reagent production, recombinant plasmids containing maximally large DNA inserts derived from chlamydial DNA were selected from the gene bank. One such plasmid is the one designed pKTH1220, which has been deposited at the culture collection Deutsche Sammlung von Microorganismen under the number (DSM 2825) and the suitability of which for use as a reagent was demonstrated by a direct hybridization test. The test showed that pKTH1220 identified all of the nucleic acids derived from different *Chlamydia trachomatis* serotypes, but no other nucleic acids.

The applicable fragments, obtainable by using different restriction enzymes, were selected from the pKTH1220-plasmid DNA, and some of these fragments were transferred by further cloning into pAT153 plasmid (Maniatis et al., Molecular Cloning. A Laboratory Manual, Cold String Harbor Laboratory, p. 6, 1982) and come to M13 phage. FIG. 10 shows the recombinant plasmid pKTH1220, having a molecular length of 14 kb. In FIG. 10, BamHI, SalI and ClaI represent the restriction enzymes used, and $a_1$, $a_2$, $b_1$, $b_2$ and $b_3$ illustrate the size and mutual locations of the fragments produced with the aid of these restriction enzymes. The fragments belonging to the series b as labeled probes. Table 1 lists the sizes of the fragments and the vectors used for further cloning, the names of the recombinant plasmids, and their use.

The fragments listed in Table 1 were isolated from an agarose gel by electroelution and were cloned into the appropriate restriction enzyme identification sites of the vectors listed in Table 1, by using known methods.

The fragment BamHI-BamHI 2.1 kb was produced as follows: the fragments BamHI-SalI 1.4kb and SalI-BamHI 0.7kb of the plasmid pKTH1220 were separated by gel electrophoresis in agarose gel, from which they were isolated. The purified fragments were joined to each other with the aid of T4 ligase enzyme, and of the 2.1 kb DNA fragments produced in the reaction, those which had free ends which were identified by the BamHI enzyme were further joined to the BamHI restriction site of the doublestranded form of the M13mp8 phage DNA. Thus there was made a recombinant phage-DNA (mKTH1245) which contains *Chlamydia trachomatis* DNA comprising two separate DNA fragments which are not located adjacently in the genome. However, in the genome they are located adjacent to the DNA reagents pKTH1250 and pKTH1252 to be affixed to the filter (FIG. 11). FIG. 11 shows an array of sandwich hybrids which is formed when the recombinant plasmids and recombinant phages listed in Table 1 are used as arrays of nucleic acid reagents.

TABLE 1

| | Fragment | Size | Vector | Recombinant plasmid | Use |
|---|---|---|---|---|---|
| $a_1$ | ClaI-SalI | 3.0 kb | pAT153 | pKTH1252 | Filter |
| $a_2$ | SalI-ClaI | 2.9 kb | pAT153 | pKTH1250 | Filter |
| $b_1$ | SalI-BamHI | 0.7 kb | M13mp8 | mKTH1242 | Labeled probe |
| $b_2$ | BamHI-SalI | 1.4 kb | M13mp8 | mKTH1239 | Labeled probe |
| $b_3$ | ClaI-ClaI | 1.7 kb | M13mp8 | mKTH1248 | Labeled probe |
| $b_1$-$b_2$ | BamHI-BamHI | 2.1 kb | M13mp8 | mKTH1245 | Labeled probe |

(b) Demonstration of the sensitivity of an array of nucleic acid reagents from *Chlamydia trachomatis* by using the sandwich hybridization method The sensitivity of an array of nucleic acid reagents as compared with a single continuous reagent pair was studied by the sandwich hybridization method. The test was carried out using filters which all contained $10^{11}$ molecules of both pKTH1250 ($a_2$) and pKTH1252 ($a_1$) DNA rendered single-stranded. The sample to be studied was the plasmid pKTH1220, which for the test was rendered single-stranded by boiling for 5 min in 0.17 M NaOH, whereafter it was transferred to 0° C. and neutralized with an equimolar amount of acetic acid. The following probes labeled with $^{125}I$, listed in Table 1, were used in the tests: mKTH1242 ($b_1$), MKTH1239 ($b_2$), MKTH1248 ($b_3$) and mKTH1245($b_1$-$b_2$).

The hybridization was performed at +65° C. for 17 hours in a hybridization solution having the following composition: 4×SSC, 0.02 % Ficoll, 0.02 % polyvinyl pyrrolidone, 0.2 % SDS, and 200 μ/ml herring sperm DNA. The filters were washed for 2 h at 50° C. with a washing solution, having the following composition: 0.1×SSC, 0.2% SDS, and were counted using a gamma-counter. The results are shown in Table 2 and are the means of five parallel tests.

TABLE 2

| Specimen molecules/test | Hybridized radioactivity, with (b) as the probe: $b_1$ | $b_2$ | $b_3$ | $b_1$, $b_2$ | ($b_1 - b_2$) | ($b_1 - b_2$), $b_3$ |
|---|---|---|---|---|---|---|
| 0 | 37 | 37 | 33 | 49 | 39 | 52 |
| $10^6$ | 48 | 44 | 48 | 93 | 68 | 140 |
| $10^7$ | 226 | 236 | 232 | 396 | 416 | 686 |
| $10^8$ | 1425 | 1415 | 1456 | 2912 | 2637 | 3580 |

| | |
|---|---|
| $b_1$ | 380,000 cpm/test; $5 \times 10^7$ cpm/μgDNA |
| $b_2$ | 340,000 cpm/test; $4 \times 10^7$ cpm/μgDNA |
| $b_3$ | 350,000 cpm/test; $5 \times 10^7$ cpm/μgDNA |
| $b_1 - b_2$ | 310,000 cpm/test; $7 \times 10^7$ cpm/μgDNA |
| $b_1$, $b_2$ | 700,000 cpm/test; |
| ($b_1 - b_2$), $b_3$ | 700,000 cpm/test; |

Statistically calculated, the 95% confidence limit of the tests performed without a sample (=negative controls) was regarded as the lower limit for positivity. These values were 52–54 cpm when the probe was $b_1$, $b_2$ or $b_3$, 58 cpm when the probe was $b_1$, $b_2$, 56 cpm when the probe was $b_1-b_2$, and 65 cpm when the probe was $b_1-b_2$, $b_3$.

(c) Chlamydia diagnostics by using sandwich hybridization with arrays of nucleic acid fragments Specimens taken from three men suffering from urethritis and three women suffering from cervicitis were selected for the test. Chlamydia trachomatis had been isolated from the male urethral specimens and the female specimens taken from the cervix. In addition, a corresponding number of similar patient specimens, from which chlamydia had not been isolated, were studied. The specimens to be examined were taken with cotton-tipped swabs which were immersed in a chlamydia sample-taking buffer containing 0.2 M saccharose, 20 mM phosphate buffer, 3% fetal calf serum, 10 µg/ml gentamicin, 100 µg/ml vancomycin, and 25 IU/ml nystatin.

Chlamydia was cultivated from the specimens. The original specimens were also assayed by sandwich hybridization using an array of nucleic acid fragments. The specimens were concentrated by using 2-butanol to remove liquid from them in such a way that the final volume was about 80 µl, their concentration for the testing thus being about 3–7 fold. Thereafter 70 mM EDTA, 0.7 % SDS, 200 ug/ml proteinase K enzyme were added to the specimen, and it was treated for 15 min at 55° C. and for 45 min at 37° C. Thereafter the specimen was boiled for 5 min in 0.175 M NaOH. The boiled specimen was transferred to 0° C. and neutralized with an equimolar amount of acetic acid and tested. The filters and hybridization conditions described in Example 1b were used in the test. The probe used was mKTH1245 ($b_1-b_2$), 300,000 cpm/400 µl hybridization reaction. The results are shown in Table 3.

TABLE 3

| Specimen | Hybridized radioactivity | Result of chlamydia culture |
|---|---|---|
| Man 1. | 151 | + |
| Man 2. | 164 | + |
| Man 3. | 154 | + |
| Man 4. | 61 | − |
| Man 5. | 76 | − |
| Man 6. | 55 | − |
| Woman 1. | 343 | + |
| Woman 2. | 509 | + |
| Woman 3. | 362 | + |
| Woman 4. | 57 | − |
| Woman 5. | 58 | − |
| Woman 6. | 81 | − |
| Buffer, $X_4$ | 30–55 | |
| Chl. trachomatis L2 bacterium, $10^6$ | 419 | + |

The limit for positivity in the test was 104 cmp.

The result in Table 3 shows that sandwich hybridization using an array of nucleic acid fragments is suitable for diagnosis venereal diseases. The samples which were negative in the culture tests were negative also in the sandwich hybridization test.

EXAMPLE 2.

(a) An array of nucleic acid reagents from Cytomegalovirus and their preparation DNA fragments suitable for the diagnostics of Cytomegalovirus were prepared from Cytomegalovirus (AD 169, ATCC VR-53S)-(CMV). DNA was isolated and fragmented by known methods. EcoRI fragment I of about 9 kb, defined in Spector et al., J. Virol. 42, 558–582, 1982, was isolated from agarose gel by electroelution after the EcoRI restriction fragments had been separated on the basis of their size. The eluted DNA was extracted with phenol, whereafter it was precipitated with ethanol. The DNA thus purified was joined by means of T4-ligase to the pBR325 plasmid vector opened by using the EcoRI enzyme, and the produced recombinant-DNA were transferred to E. coli. K12 HB101 host bacteria. From among ampicillin and tetracyclin resistent but chloramphenicol sensitive clones there was selected one which contained a cytomegalovirus-specific DNA insert of the correct size. The character of the cloned cytomegalovirus DNA was ascertained by the Southern blot method. This test ensured that the described 9 kb EcoRI-DNA fragment was derived from the DNA of Cytomegalovirus and, more specifically, was included in its HindIII-D fragment (Oram et al., J. Gen. Virol., 59, 111–129, 1982). The recombinant plasmid thus described was designated pKTH1271, and it was deposited at the culture collection Deutsche Sammlung von Microorganismen under number DSM 2826. The recombinant plasmid was grown and purified by known techniques.

Figures 12, 13:
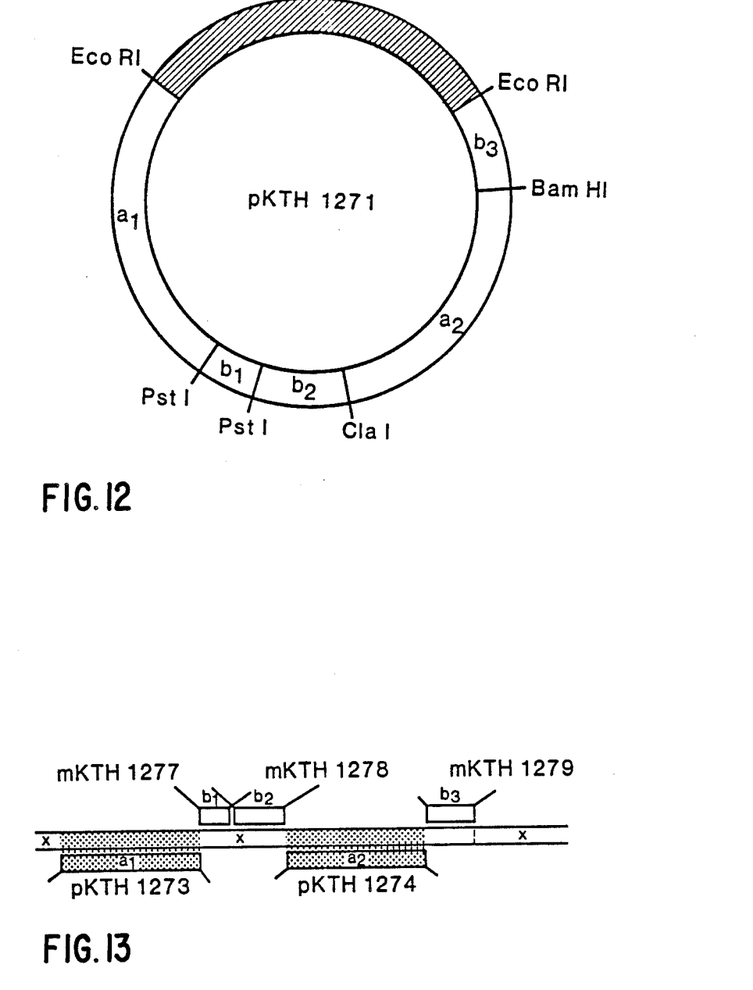
FIG. 12 shows the recombinant plasmid pKTH1271.
FIG. 13 shows an array of sandwich hybrids which is formed when arrays of nucleic acid fragments prepared from the recombinant plasmid pKTH1271 are used. Our invention relates to nucleic acid reagents composed of an array of nucleic acid fragments. These arrays of nucleic acid reagents comprise at least two, but preferably several, alternating nucleic acid fragments, up to 20 fragments, which are derived from one or several nucleic acids sufficiently homologous to the nucleic acid which is to be identified. Thereby there are obtained at least two series of alternating arrays of nucleic acid fragments, which must not be homologous to one another.

The further clonings were carried out by known techniques by using as vectors the pBR322 plasmid and the M13mp7 and M13mp8 phages. FIGS. 12 shows the hybrid plasmid pKTH1271 having a molecular length of about 9 kb. The array of nucleic acid fragments shown in FIG. 12 were prepared by using the restriction enzymes EcoRI, BamHI, ClaI and PstI. FIG. 12 shows the fragments obtained by using the restriction enzymes as well as their relative size and location. Table 4 lists the sizes of the fragments in question and the vectors used for the further cloning, the names of the thus obtained recombinant plasmids, and their use either as filter reagents or as labeled probes. FIG. 13 shows an array of sandwich hybrids which is formed when the array of nucleic acid fragments listed in Table 4 are used.

TABLE 4

| | Restriction | fragment | Vector | Designation | Use |
|---|---|---|---|---|---|
| $a_1$ | EcoRI-PstI | (3.3 kb) | pBR322 | pKTH1273 | Filter |
| $a_2$ | ClaI-BamHI | (3.0 kb) | pBR322 | pKTF1274 | Filter |
| $b_1$ | PstI-PstI | (0.6 kb) | M13mp7 | mKTH1277 | Labeled probe |
| $b_2$ | PstI-ClaI | (1.0 kb) | M13mp8 | mKTH1278 | Labeled probe |
| $b_3$ | BamHO-EcoRI | (1.0 kb) | M13mp8 | mKTH1279 | Labeled probe |

(b) Demonstration of the sensitivity of an array nucleic acid reagents from cytomegalovirus by the sandwich hybridization method The sensitivity of an array of nucleic acid reagents as compared with one continuous reagent pair was assayed by the sandwich hybridization method. The specimen in the tests was CMV DNA, which was boiled in 0.17M NaOH for 5 min. and was thereafter neutralized as in example 1b. Filters which all contained $10_{11}$ molecules of both pKTH1273($a_1$) DNA and pKTH1274($a_2$) DNA, rendered single-stranded, and the following probes labeled with $^{125}$I listed in Table 4: mKTH1277 ($b_1$), mKTH1278($b_2$) and mKTH1279($b_3$) were used in the test. The probes each contained $10^8$ cpm/µg DNA. The hybridization was carried out as described in Example 1b. The results are shown in Table 5.

TABLE 5

| Specimen molecules/test | Hybridized radioactivity, with (b) as the probe | | | | |
|---|---|---|---|---|---|
| | $b_1$ | $b_2$ | $b_3$ | $b_1, b_2$ | $b_1, b_2, b_3$ |
| 0 | 35 | 33 | 38 | 45 | 53 |
| $10^6$ | 38 | 44 | 46 | 95 | 125 |
| $4 \times 10^6$ | 85 | 135 | 142 | 205 | 292 |
| $1.6 \times 10^7$ | 203 | 254 | 265 | 415 | 645 |
| $b_1$ | 310.000 cpm/test | | | | |
| $b_2$ | 320.000 cpm/test | | | | |
| $b_3$ | 300.000 cpm/test | | | | |
| $b_1, b_2$ | 300.000 cpm of each/test | | | | |
| $b_1, b_2, b_3$ | 300.000 cpm of each/test | | | | |

In the test of value of the lower limit for positive was 51–55 cpm when the probe was $b_1$, $b_2$ or $b_3$, 59 cpm when the probe was $b_1$, $b_2$, and 63 cpm when the probe was $b_1$, $b_2$, $b_3$ The results in Table 5 show that sandwich hybridization in which an individual probe reagent in used ($b_1$, $b_2$ or $b_3$) detects in each case $4 \times 10^6$ CMV-DNA molecules. On the other hand, hybridization with a reagent of $b_1$, $b_2$ or $b_1$, $b_2$, $b_3$ detects as few as $10^6$ molecules of CMV-DNA. The results show that the array of nucleic acid reagents are four times as sensitive as individual nucleic acid reagents.

(c) CMV diagnostics by using sandwich hybridization with an array of nucleic acid reagents Clinical spcimens were assayed by using sandwich hybridization with an array of reagents. These samples included two urine specimens from children under 1 year. These children were suspected of suffering from a congenital cytomegalo disease. A lung biopsy specimen from a patient with CMV pulmonary infection was also assayed by the present sandwich hybridization. Both cytomegalovirus-infected and uninfected human fetal cells were also used as specimens in the test.

A solution which contained 1 % sarcosyl and 5 mM EDTA and 200 μg calf thymus DNA was added to a 10 ml urine specimen, whereafter the DNA released from the virus, together with the carrier, was precipitated using 10 ml isopropanol at room temperature. The DNA precipitate was dissolved in 200 μl of TE buffer and was brought to a single-stranded form by boiling it for 5 min, whereafter the DNA solution was cooled to 0° C. and added to the hybridization solution.

The lung biopsy specimen (a few mm$^3$) was minced mechanically, with a knife, 200 μl of TE buffer containing 1% SDS solution and 1 mg/ml of proteinase K-enzyme was added to it. A digestion was carried out at +37° C. for 1 h whereafter the specimen was drawn into an injection syringe twice through a thin hypodermical needle. The specimen thus homogenized was boiled, whereafter it was added to the test solution.

The cells infected with cytomegalovirus and the uninfected cells were broken up by an SDS, proteinase K treatment, homogenized and boiled, as above.

The reagents in the hybridization test were pKTH1273($a_1$) and pKTH1274($a_2$) on filters and mKTH1277($b_1$), mKTH1278($b_2$), mKTH1279($b_3$) as probes, each 200.000 cpm/reaction. In other respects the hybridization, the washing of the filters and the counting of the results were carried out as described in Example 1b.

The results of the present hybridization are shown in Table 6.

TABLE 6

| Specimen | Hybridized radioactivity | Virus isolation |
|---|---|---|
| Infected cells ($10^5$) | 3521 | Not done |
| Urine 1 (10 ml) | 243 | CMV |
| Urine 2 (10 ml) | 3215 | CMV |
| Urine from a healthy person (10 ml) | 52 | Not done |
| Lung biopsy specimen | 535 | CMV |
| Control cells $10^5$ | 68 | Not done |
| No specimen | 65 | Not done |

The results in Table 6 show that it is possible, by using an array of nucleic acid reagents, to demonstrate CMV in different clinical specimens such as urine, lung biopsy specimens and cells.

The test is specific to cytomegalovirus; it does not identify human DNA, i.e. the test is not interfered by the human DNA present in the sample. In fact the type of specimen does not interfere with the specifity of test in any way.

What is claimed is:

1. A nucleic acid reagent for use in a sandwich hybridization array to detect the identity of a nucleic acid, said nucleic acid reagent comprising at least two sets of at least two alternating nucleic acid fragments which are homologous to the nucleic acid which is to be identified, said alternating nucleic acid fragments being not homologous to one another, wherein at least one of the sets of nucleic acid fragments are labeled and at least one set of nucleic acid fragments are affixed to a solid carrier.

2. The nucleic acid reagent according to claim 1, wherein some or all of the nucleic acid fragments on one or more of the sets of nucleic acid fragments are joined to form an array of nucleic acid fragments.

3. The nucleic acid reagent according to claim 2, comprising nucleic acid fragments which have vector-derived parts.

4. The nucleic acid reagent according to claim 2, comprising the recombinant plasmid pKTH1271 or derivatives thereof, which recombinant plasmid contains the DNA of Cytomegalovirus Ad169 and is cloned into the host *Escherichia coli* K12 HB101, and the deposit number of said host containing the recombinant plasmid pKTH1271 is DSM 2826.

5. The nucleic acid reagent according to claim 2, comprising nucleic acid fragments which have vector-derived parts.

6. The nucleic acid reagent according to claim 1, comprising the recombinant plasmid pKTH1271 or derivatives thereof, which recombinant plasmid contains the DNA of Cytomegalovirus AD169 and is cloned into the host *Escherichia coli* K12 HB101, and the deposit number of said host containing the recombinant plasmid pKTH1271 DSM 2826.

7. Nucleic acid reagents comprising arrays of alternating nucleic acid fragments comprising the recombinant plasmid pKTH1220 or its derivatives and which recombinant plasmid contains the DNA of Chlamydia trachomatis L2 bacterium and is cloned into the host *Escherichia coli* K12, HB101, and the deposit number of this host comprising the recombinant plasmid pKTH1220 is DSM 2825.

8. Nucleic acid reagent comprising two or more series of at least two alternating arrays of nucleic acid fragments sufficiently homologous to the nucleic acid which is to be identified but not homologous to one another, comprising the recombinant plasmid pKTH1220 or its derivatives and which recombinant plasmid contains the DNA of *Chlamydia trachomatis* L2 bacterium and is cloned into the host *Escherichia coli* K12, HB101, and the deposit number of this host comprising the recombinant plasmid pKTH1220 is DSM 2825.

9. A method for identifying more than one nucleic acid comprising exposing the nucleic acids to the nucleic acid reagent according to claim 2, wherein combinations of nucleic acid reagents are assembled from nucleic acid fragments which are homologous to the nucleic acids to be identified.

10. A method for the preparation of the nucleic acid reagent according to claim 2, wherein the nucleic acid reagent is prepared synthetically, semi-synthetically or by using recombinant-DNA techniques.

11. The method according to claim 10, wherein the preparation of the nuclei acid reagent comprises:

(a) isolating nucleic acids which are homologous to the nucleic acids to be identified;
(b) cloning said nucleic acids into vectors;
(c) fragmenting said nucleic acids using restriction enzymes into at least two sets of at least two alternating nucleic acid fragments;
(d) cloning said nucleic acid fragments into vectors;
(e) labeling one set of nucleic acid fragments; and
(f) fixing said nucleic acid fragments belonging to a second set of nucleic acid fragments to a solid carrier.

12. The method according to claim 11, wherein after step (c), some or all of the nucleic acid fragments are combined to form arrays of nucleic acids by using suitable ligases.

13. The method according to claim 11, wherein in step (d) the fragments belonging to different sets are cloned into different vectors.

14. A method for identifying more than one nucleic acid comprising exposing the nucleic acids to the nucleic acid reagent according to claim 1, wherein combinations of nucleic acid reagents are assembled from nucleic acid fragments which are homologous to the nucleic acids to be identified.

15. A method for the preparation of the nucleic acid reagent according to claim 1, wherein the nucleic acid reagent is prepared synthetically,semi-synthetically or by using recombinant-DNA techniques.

16. The method according to claim 15 wherein the preparation of the nucleic acid reagent comprises:

(a) isolating nucleic acids which are homologous to the nucleic acids to be identified;
(b) cloning said nucleic acids into vectors;
(c) fragmenting said nucleic acids using restriction enzymes into at least two sets of at least two alternating nucleic acid fragments;
(d) cloning said nucleic acid fragments into vectors;
(e) labeling one set of nucleic acid fragments; and
(f) fixing said nucleic acid fragments belonging to a second set of nucleic acid fragments to a solid carrier.

17. The method according to claim 16, wherein in step (d) the fragments belonging to different sets are cloned into different vectors.

18. A method for conducting a sandwich hybridization array using a nucleic acid reagent to detect the identity of a nucleic acid, said method comprising exposing said nucleic acid to said nucleic acid reagent, said nucleic acid reagent comprising at least two sets of at least two alternating nucleic acid fragments which are homologous to the nucleic acid which is to be identified, said nucleic acid fragments being not homologous to one another, wherein the nucleic acid fragments from each of said sets alternate in said nucleic acid reagent and at least one of said sets of nucleic acid fragments are labeled and at least one set of nucleic fragments are affixed to a solid carrier.

19. The method according to claim 18, wherein some or all of the nucleic acid fragments on one or more of the sets of nucleic acid fragments are joined ot form an array of nucleic acid fragments.

20. The method according to claim 18, comprising nucleic acid fragments which have vector-derived parts.

21. The method according to claim 18, comprising the recombinant plasmid pKTH1220 or derivatives thereof, which recombinant plasmid contains the DNA of *Chlamydia trachomatis* L2 bacterium and is cloned into the host *Escherichia coli* K12 HB101, and the deposit number of said host containing the recombinant plasmid pKTH1220 is DSM 2825.

22. The method according to claim 18, comprising the recombinant plasmid pKTH1271 or derivatives thereof, which recombinant plasmid contains the DNA of Cytomegalovirus AD169 and is cloned into the host *Escherichia coli* $K_{12}$ HB101, and the eposit number of said host containing the recombinant plasmid KTH1271 is DSM 2826.

* * * * *